United States Patent
Srinivasan et al.

(10) Patent No.: US 8,208,146 B2
(45) Date of Patent: Jun. 26, 2012

(54) DROPLET ACTUATOR DEVICES, CONFIGURATIONS, AND METHODS FOR IMPROVING ABSORBANCE DETECTION

(75) Inventors: Vijay Srinivasan, Durham, NC (US); Vamsee K. Pamula, Durham, NC (US); Michael G. Pollack, Durham, NC (US); Tih-Hong Wang, Cary, NC (US)

(73) Assignee: Advanced Liquid Logic, Inc., Research Triangle Park, NC (US)

( * ) Notice: Subject to any disclaimer, the term of this patent is extended or adjusted under 35 U.S.C. 154(b) by 309 days.

(21) Appl. No.: 12/529,025

(22) PCT Filed: Mar. 13, 2008

(86) PCT No.: PCT/US2008/056797
§ 371 (c)(1),
(2), (4) Date: Aug. 28, 2009

(87) PCT Pub. No.: WO2008/112856
PCT Pub. Date: Sep. 18, 2008

(65) Prior Publication Data
US 2010/0118307 A1    May 13, 2010

Related U.S. Application Data

(60) Provisional application No. 60/894,506, filed on Mar. 13, 2007, provisional application No. 60/980,363, filed on Oct. 16, 2007.

(51) Int. Cl.
*G01N 21/00* (2006.01)
*G01N 35/00* (2006.01)

(52) U.S. Cl. ............ 356/436; 356/432; 356/437; 422/62

(58) Field of Classification Search .......... 356/432–437; 250/459.1, 458.1; 437/19; 422/82.05, 81, 422/89; 435/6, 91.1, 91.2
See application file for complete search history.

(56) References Cited

U.S. PATENT DOCUMENTS

| 3,734,622 | A | * | 5/1973 | Adler ............................ 356/338 |
| 4,867,559 | A |   | 9/1989 | Bach |
| 6,294,063 | B1 |   | 9/2001 | Becker et al. |
| 6,338,820 | B1 | * | 1/2002 | Hubbard et al. ................. 422/64 |
| 7,544,955 | B2 | * | 6/2009 | Boutet ......................... 250/459.1 |
| 7,727,723 | B2 | * | 6/2010 | Pollack et al. ................ 435/6.11 |
| 7,815,871 | B2 | * | 10/2010 | Pamula et al. ................. 422/404 |
| 7,822,510 | B2 | * | 10/2010 | Paik et al. ...................... 700/283 |
| 2005/0078138 | A1 | * | 4/2005 | Koyama .......................... 347/19 |
| 2005/0112541 | A1 | * | 5/2005 | Durack et al. ..................... 435/2 |
| 2006/0039823 | A1 |   | 2/2006 | Yamakawa et al. |
| 2006/0105469 | A1 |   | 5/2006 | Lea et al. |
| 2006/0254933 | A1 |   | 11/2006 | Adachi et al. |
| 2007/0159609 | A1 | * | 7/2007 | Takaiwa et al. ................. 355/53 |

FOREIGN PATENT DOCUMENTS

JP    2-236147 A    9/1990
WO    2006124458 A2    11/2006

OTHER PUBLICATIONS

Moon, Hyejin, Ph.d., "Electrowetting-on-dielectric microfluidics: Modeling, physics, and MALDI application," University of California, Los Angeles, 2005, 122 pages.

(Continued)

*Primary Examiner* — Sang Nguyen
(74) *Attorney, Agent, or Firm* — William A. Barrett; Ward & Smith, PA

(57) ABSTRACT

Devices, configurations and methods for improving absorbance detection are provided. For example, methods and devices are provided for determining the absorbance of a droplet, e.g., a droplet on a droplet actuator, by providing an elongated light path through the droplet.

12 Claims, 14 Drawing Sheets

OTHER PUBLICATIONS

Jie Ding, "System level architectural optimization of semi-reconfigurable microfluidic system," M. S. Thesis, Duke University Dept of Electrical Engineering, 2000.

Pollack et al., "Electrowetting-Based Actuation of Droplets for Integrated Microfluidics," Lab on a Chip (LOC), vol. 2, pp. 96-101, 2002.

Pollack et al., "Electrowetting-based actuation of liquid droplets for microfluidic applications," Appl. Phys. Letters, vol. 77, No. 11 (Sep. 11, 2000), pp. 1725-1726.

Vijay Srinivasan, Vamsee K. Pamula, Richard B. Fair, "An integrated digital microfluidic lab-on-a-chip for clinical diagnostics on human physiological fluids," Lab on a Chip (LOC), vol. 4, pp. 310-315, 2004.

* cited by examiner

DROPLET ACTUATOR DEVICES, CONFIGURATIONS, AND METHODS FOR IMPROVING ABSORBANCE DETECTION

2 RELATED APPLICATIONS

This patent application claims priority to U.S. Patent Application Nos. 60/894,506, filed on Mar. 13, 2007, and 60/980,363 filed on Oct. 16, 2007, both entitled "Droplet actuator with improved absorbance detection," the entire disclosures of which are incorporated herein by reference.

1 GRANT INFORMATION

This invention was made with government support under DK066956-02 and GM072155-02 awarded by the National Institutes of Health of the United States. The United States Government has certain rights in the invention.

3 FIELD OF THE INVENTION

The invention relates to droplet actuator devices, configurations and methods for improving absorbance detection of a droplet on the droplet actuator.

4 BACKGROUND OF THE INVENTION

Droplet actuators are used to conduct a wide variety of droplet operations. A droplet actuator typically includes a substrate associated with electrodes configured for conducting droplet operations on a droplet operations surface thereof and may also include a second substrate arranged in a generally parallel fashion in relation to the droplet operations surface to form a gap in which droplet operations are effected. The gap is typically filled with a filler fluid that is immiscible with the fluid that is to be subjected to droplet operations on the droplet actuator. In some applications, it is useful to detect absorbance of a droplet or other fluid, and in some cases, the fluid is located on a droplet actuator. There is a need in the art for improved droplet actuator devices and methods for this purpose.

5 BRIEF DESCRIPTION OF THE INVENTION

The invention relates to a device for determining the absorbance of a droplet. The device may be a droplet actuator device. The invention also relates to methods of making and using the device.

The invention may make use of a droplet actuator. The droplet actuator may include two substrates separated to form a gap. A droplet positioned in the gap will have a droplet height established by surfaces of the two substrates. A light source may be arranged to transmit light through the droplet. A sensor may be arranged to sense light emitted from the droplet. In this manner, a light path is established from the light source, through the droplet, to the sensor. In operation, a method of the invention involves directing light from the light source through the droplet and to the sensor; sensing the light energy at the sensor; and determining from the sensed light energy an optical property of the droplet.

In some embodiments, the light path through the droplet is greater than the droplet height. The light path may, for example, be substantially parallel with the surfaces of the substrates. The light path through the droplet may, in some cases, be substantially perpendicular to the droplet height. In other cases, the light path through the droplet may be established at an angle that is substantially acute with respect to one of the surfaces establishing the droplet height.

In various embodiments, the light source and the sensor are offset from a central vertical axis of the droplet. The light source and the sensor may be arranged on the same or opposite sides of a droplet actuator. In some embodiments, the light path through the droplet is at least 2, 3, 4, 5, 6, 7, 8, 9, 10 or more times greater than the droplet height.

In certain embodiments, one or more of the substrates comprises a recessed region such that a droplet located in the recessed region has a greater droplet height than a droplet located in a region that is not so recessed. In other cases, one or more of the substrates comprises an aperture arranged such that a droplet in contact with the aperture will enter the aperture, thereby providing the droplet with a greater droplet height than a droplet located in the gap.

Droplet operations may be used to elongate or increase the height of the droplet along the direction of the light path. The droplet operations may, in some cases, be mediated by electrodes. The droplet may be positioned within an aperture of a substrate, thereby increasing the droplet height or length.

One or more electrodes may be provided in one or more of the substrates and configured to conduct one or more droplet operations elongating the droplet in a manner which increases the distance of the light path through the droplet.

Various optical elements may be interposed between the light source and the droplet and/or between the droplet and the sensor. Diffractive material may be used to direct light from the light source through the droplet and to the sensor. For example, the light path may be directed through the diffractive material prior to or after the droplet. As examples, a prism or waveguide may be provided as the diffractive material.

In other embodiments the light path may reflect off of a surface of one or both of the two substrates. In some cases, one or more of the substrates may include a material having a lower refractive index than the droplet.

In various embodiments, the droplets subjected to detection may include beads. The optical property of the droplet may be indicative of an optical property of the beads. In other embodiments, the droplet may include biological cells, and the optical property of the droplet may be indicative of an optical property of the biological cells.

Further in various embodiments, the droplet subjected to detection may be partially or completely surrounded by filler fluid. The filler fluid may, in some cases, have different light refractive characteristics than light refractive characteristics of the droplet. For example, the filler fluid may be selected such that certain wavelengths of light incident upon the filler fluid do not reach the sensor. As another example, light in a wavelength of interest may pass through the droplet to the sensor but may not pass through the filler fluid to the sensor.

Various other embodiments of the invention will be apparent from the detailed description, definitions, claims and figures.

6 DEFINITIONS

As used herein, the following terms have the meanings indicated.

"Activate" with reference to one or more electrodes means effecting a change in the electrical state of the one or more electrodes which results in a droplet operation.

"Bead," with respect to beads on a droplet actuator, means any bead or particle that is capable of interacting with a droplet on or in proximity with a droplet actuator. Beads may be any of a wide variety of shapes, such as spherical, generally spherical, egg shaped, disc shaped, cubical and other three dimensional shapes. The bead may, for example, be capable of being transported in a droplet on a droplet actuator or otherwise configured with respect to a droplet actuator in a manner which permits a droplet on the droplet actuator to be brought into contact with the bead, on the droplet actuator and/or off the droplet actuator. Beads may be manufactured using a wide variety of materials, including for example, resins, and polymers. The beads may be any suitable size, including for example, microbeads, microparticles, nanobeads and nanoparticles. In some cases, beads are magnetically responsive; in other cases beads are not significantly magnetically responsive. For magnetically responsive beads, the magnetically responsive material may constitute substantially all of a bead or one component only of a bead. The remainder of the bead may include, among other things, polymeric material, coatings, and moieties which permit attachment of an assay reagent. Examples of suitable magnetically responsive beads are described in U.S. Patent Publication No. 2005-0260686, entitled, "Multiplex flow assays preferably with magnetic particles as solid phase," published on Nov. 24, 2005, the entire disclosure of which is incorporated herein by reference for its teaching concerning magnetically responsive materials and beads. The beads may include one or more populations of biological cells adhered thereto. In some cases, the biological cells are a substantially pure population. In other cases, the biological cells include different cell populations, e.g., cell populations which interact with one another.

"Droplet" means a volume of liquid on a droplet actuator that is at least partially bounded by filler fluid. For example, a droplet may be completely surrounded by filler fluid or may be bounded by filler fluid and one or more surfaces of the droplet actuator. Droplets may take a wide variety of shapes; nonlimiting examples include generally disc shaped, slug shaped, truncated sphere, ellipsoid, spherical, partially compressed sphere, hemispherical, ovoid, cylindrical, and various shapes formed during droplet operations, such as merging or splitting or formed as a result of contact of such shapes with one or more surfaces of a droplet actuator.

"Droplet operation" means any manipulation of a droplet on a droplet actuator. A droplet operation may, for example, include: loading a droplet into the droplet actuator; dispensing one or more droplets from a source droplet; splitting, separating or dividing a droplet into two or more droplets; transporting a droplet from one location to another in any direction; merging or combining two or more droplets into a single droplet; diluting a droplet; mixing a droplet; agitating a droplet; deforming a droplet; retaining a droplet in position; incubating a droplet; heating a droplet; vaporizing a droplet; cooling a droplet; disposing of a droplet; transporting a droplet out of a droplet actuator; other droplet operations described herein; and/or any combination of the foregoing. The terms "merge," "merging," "combine," "combining" and the like are used to describe the creation of one droplet from two or more droplets. It should be understood that when such a term is used in reference to two or more droplets, any combination of droplet operations sufficient to result in the combination of the two or more droplets into one droplet may be used. For example, "merging droplet A with droplet B," can be achieved by transporting droplet A into contact with a stationary droplet B, transporting droplet B into contact with a stationary droplet A, or transporting droplets A and B into contact with each other. The terms "splitting," "separating" and "dividing" are not intended to imply any particular outcome with respect to size of the resulting droplets (i.e., the size of the resulting droplets can be the same or different) or number of resulting droplets (the number of resulting droplets may be 2, 3, 4, 5 or more). The term "mixing" refers to droplet operations which result in more homogenous distribution of one or more components within a droplet. Examples of "loading" droplet operations include microdialysis loading, pressure assisted loading, robotic loading, passive loading, and pipette loading.

The terms "top" and "bottom" are used throughout the description with reference to the top and bottom substrates of the droplet actuator for convenience only, since the droplet actuator is functional regardless of its position in space.

When a given component, such as a layer, region or substrate, is referred to herein as being disposed or formed "on" another component, that given component can be directly on the other component or, alternatively, intervening components (for example, one or more coatings, layers, interlayers, electrodes or contacts) can also be present. It will be further understood that the terms "disposed on" and "formed on" are used interchangeably to describe how a given component is positioned or situated in relation to another component. Hence, the terms "disposed on" and "formed on" are not intended to introduce any limitations relating to particular methods of material transport, deposition, or fabrication.

When a liquid in any form (e.g., a droplet or a continuous body, whether moving or stationary) is described as being "on", "at", or "over" an electrode, array, matrix or surface, such liquid could be either in direct contact with the electrode/array/matrix/surface, or could be in contact with one or more layers or films that are interposed between the liquid and the electrode/array/matrix/surface.

When a droplet is described as being "on" or "loaded on" a droplet actuator, it should be understood that the droplet is arranged on the droplet actuator in a manner which facilitates using the droplet actuator to conduct one or more droplet operations on the droplet, the droplet is arranged on the droplet actuator in a manner which facilitates sensing of a property of or a signal from the droplet, and/or the droplet has been subjected to a droplet operation on the droplet actuator.

7 BRIEF DESCRIPTION OF THE DRAWINGS

8 DETAILED DESCRIPTION OF THE INVENTION

Droplet actuators may be coupled to and/or configured with a light source and a detector. Light from the light source may pass through a droplet on the droplet actuator to the detector. Characteristics of the light energy emitted from the droplet may be detected and analyzed. For example, one can calculate the concentration of a solution based on the incident light and the intensity of light detected using Beer's law. However, for path-lengths of less than 1 cm, the effect of minor inaccuracies in the measurement of the detected light are magnified. Sensitivity is very important, and it is desirable for the change in signal to be several times larger than the noise in the solution. In droplet actuators, path-lengths of less than 1 cm are frequently observed under standard assay conditions and device placement. For example, the droplet actuator size may be hundreds of microns. Accordingly, the invention provides a device, device configuration, and/or method, in which the path-length is increased relative to the height of the droplet on the droplet actuator. The invention provides a droplet actuator configured for improved absorbance detection of a droplet or fluid on the droplet actuator.

In a standard design, the droplet is positioned between the light source and a detector, where the light source is at the bottom, the sample is in the middle, and the detector is on top. However, in the droplet actuator, the path-length in this standard design would be hundreds of microns, which, as described above is not optimal. FIGS. 1-11 illustrate improvements of the invention on the standard design.

Figure 1:
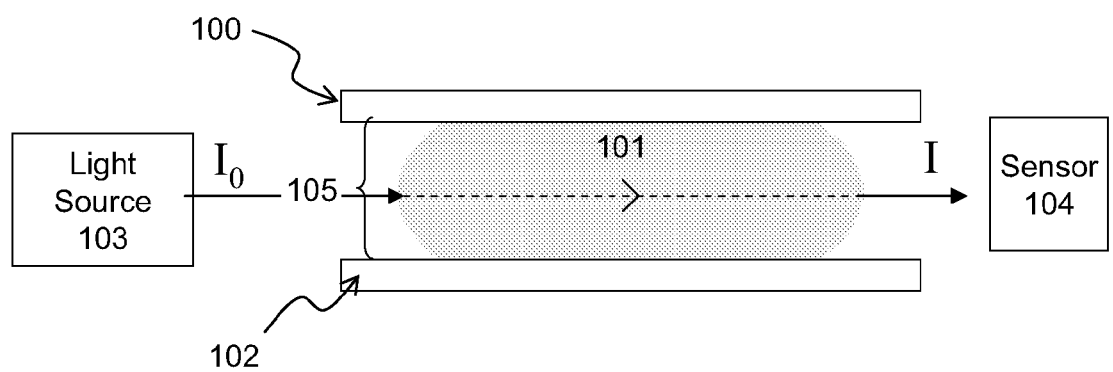
FIG. 1 illustrates an absorbance detection device or configuration of the invention in which horizontal light transmission is illustrated.

FIG. 1 illustrates an absorbance detection device or configuration of the invention. FIG. 1 shows top substrate 100 separated from bottom substrate 102 by gap 105. Gap 105 contains droplet 101. Gap 105 may typically have a gap height ranging from about 100 to about 200 µm. In other cases, the gap height can range from a few microns to several millimeters. Droplet 101 has a horizontal diameter, which may typically range from about 500 to about 1000 µm. In other cases, the horizontal diameter can range from a few microns to several millimeters. In the embodiment illustrated, the path-length of light from light source 103 as it passes through droplet 101 to detector or sensor 104 is increased relative to the gap height. Instead of light being transmitted through the shorter vertical dimension of droplet 101, it is transmitted through the greater horizontal diameter. The greater horizontal diameter results from the aspect ratio of the disc shaped droplet 101, in which the droplet height is established by the gap height. The horizontal arrangement of source 103 and detector 104 illustrated in this figure may result in about a 4.5× or 5× increase in path-length for a single droplet relative to a typical vertical configuration in a typical droplet actuator. The horizontal droplet length may in some cases be extended, for example, by forcing droplet 101 into a narrower gap and/or by forcing droplet 101 between lateral barriers, and/or by forcing droplet 101 into a capillary.

Figure 2A:
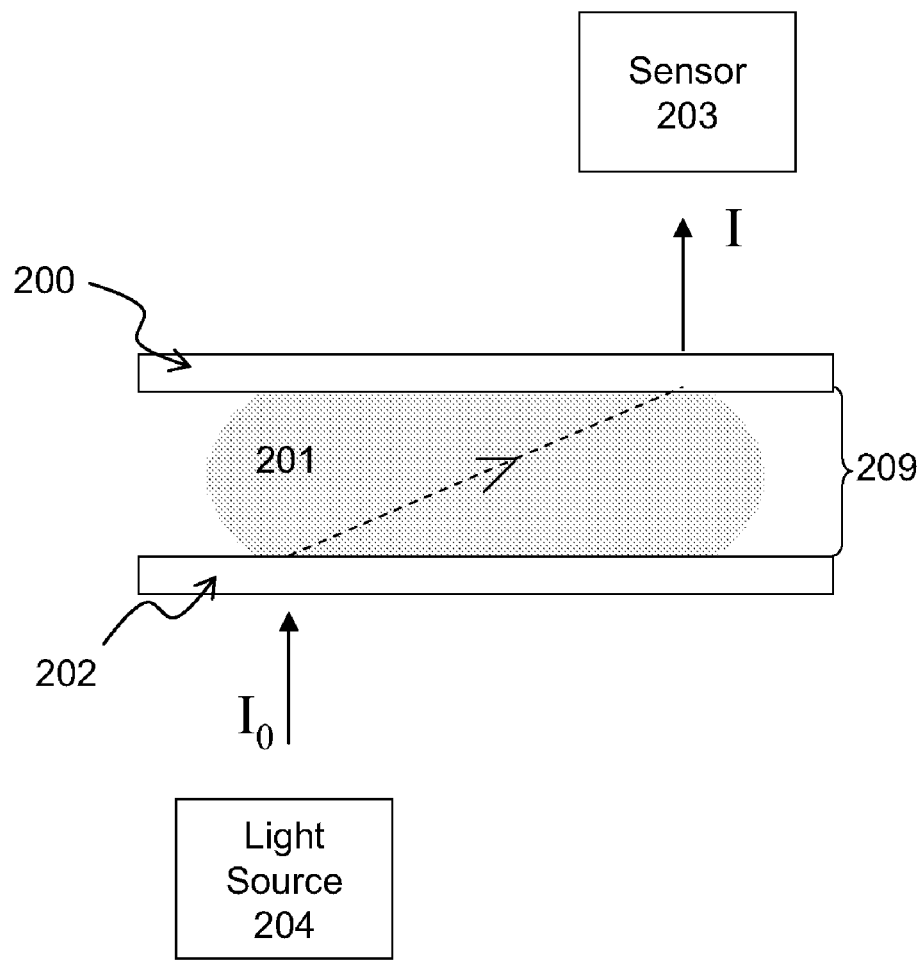
FIGS. 2A and 2B illustrate configurations of an absorbance detection device or configuration of the invention in which the light source and detector are located on opposite sides of the droplet actuator in a vertically off-set arrangement.

FIG. 2A illustrates an absorbance detection device or configuration of the invention. Top substrate 200 is separated from bottom substrate 202 by gap 209. Gap 209 may contain droplet 201. Light source 204 and detector or sensor 203 are on opposite sides of the droplet actuator. They are also off-set, i.e., they are not on the same vertical axis. In some cases, they may be on opposite sides of the same vertical axis which passes vertically through the center of droplet 201. In some embodiments, they are offset by a distance which substantially maximizes the path-length of light through droplet 201. Light is thus transmitted in a generally diagonal direction through droplet 201. The diagonal path-length is a greater path-length as compared to the height. The path-length of light through the droplet may in some cases range from about 500 to about 1000 µm.

Figure 2B:
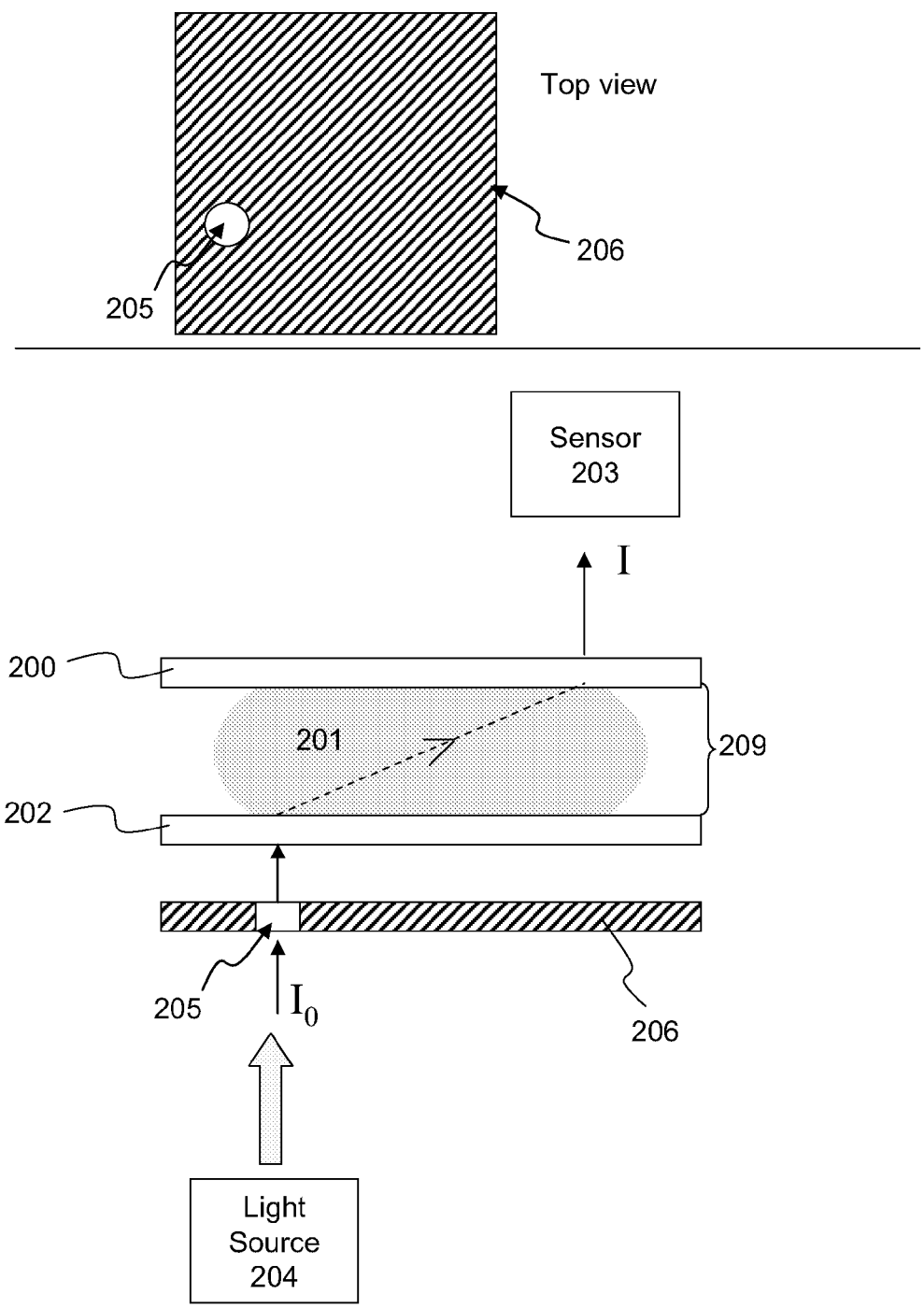

FIG. 2B illustrates an embodiment of FIG. 2A. Typically light sources are much larger than droplet size. An aperture or a mask may be provided to help ensure that all of the light from source 204 that is sensed by the sensor 203 is transmitted through droplet 201. In other words, this approach minimizes or substantially eliminates light from light source 204 reaching sensor 203 by a path that excludes droplet 201. The source 204 may be masked, the substrates of the droplet actuator may be masked, or a fiber optic with a small diameter may be used to direct light to the droplet. In the example illustrated, the masking is provided by electrode 206. Opening 205 is provided in electrode 206. Opening 205 directs light through droplet 201. The top portion of FIG. 2B represents a top view of electrode 206 showing opening 205. Opening 205 may, in some cases, be located at a position which is near an outer edge of droplet 201. The lower portion of FIG. 2B represents a side view of the droplet actuator. Light from light source 204 is transmitted through opening 205 in electrode 206, through the droplet, to the sensor.

Figure 3:
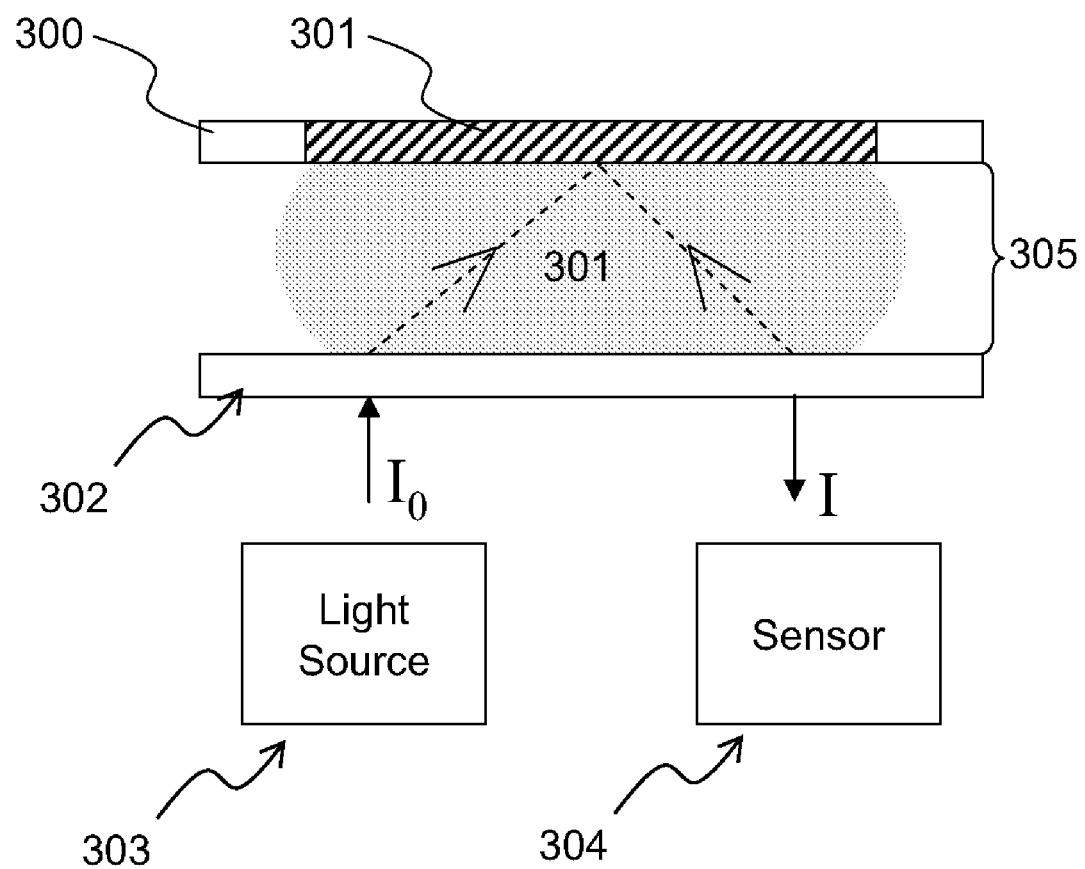
FIG. 3 illustrates an absorbance detection device or configuration of the invention in which a reflective region is utilized on one substrate.

FIG. 3 illustrates an absorbance detection device or configuration of the invention. Top surface 300 may include reflective region 301 or in some cases, the entire top surface may be reflective. Light source 303 and detector or sensor 304 are located on the same side of droplet 301. They may in some cases be located in substantially the same plane on the same side of droplet 301. Top substrate 300 includes a reflective region 301 and is separated from bottom substrate 302 by a gap 305. Alternatively, reflective region 301 may be the bottom surface. Gap 305 may contain droplet 301. Light source 303 is on the same side of droplet 301 as sensor 304 and may in some cases be in substantially the same plane as sensor 304. Reflective region 301 be rendered reflective by using reflective materials and/or coating with reflective materials, such as aluminum, gold, reflective chrome or any other reflective coating. The light transmitted by light source 303 is reflected off of reflective region 301, effectively doubling the path length of light through the droplet. Reflective region 301 may be substantially 100% reflective or may reflect only selected bandwidths of light.

Figure 4A:
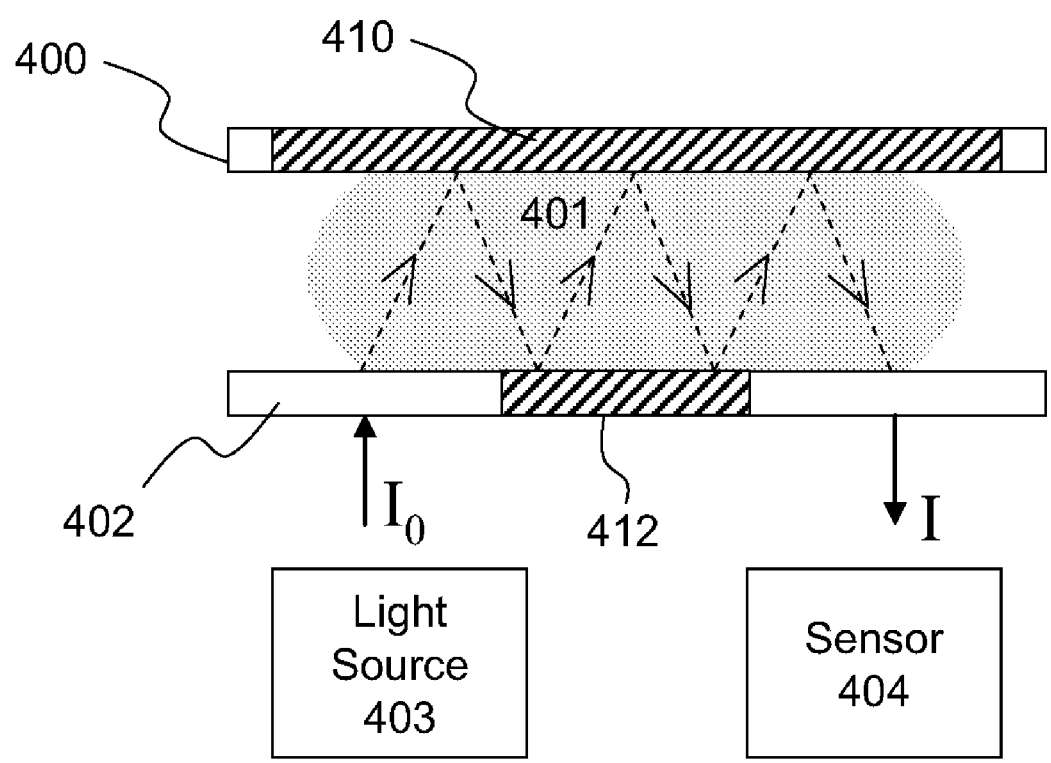
FIGS. 4A-4C illustrate various configurations of an absorbance detection device or configuration of the invention in which reflective regions are utilized on two substrates.

FIG. 4A illustrates an absorbance detection device or configuration of the invention. Both top substrate 400 and bottom substrate 402 include reflective regions 410 and 412, respectively. Light source 403 and detector or sensor 404 are located on the same side of droplet 401. Reflective surface 412 leaves sufficient opening for light to enter the droplet at one region thereof and leave the droplet at another region thereof. Preferably the distance between entry and exit points is substantially maximized. Reflective surface 410 substantially covers the droplet in order to minimize light loss via the top substrate. Light transmitted from light source 403 enters droplet 401 through bottom substrate 402. The light is reflected off of reflective surfaces 410 and 412 through droplet 401, and exits droplet 401 to sensor 404. The top and bottom substrates may be reversed in this example.

Figure 4B:
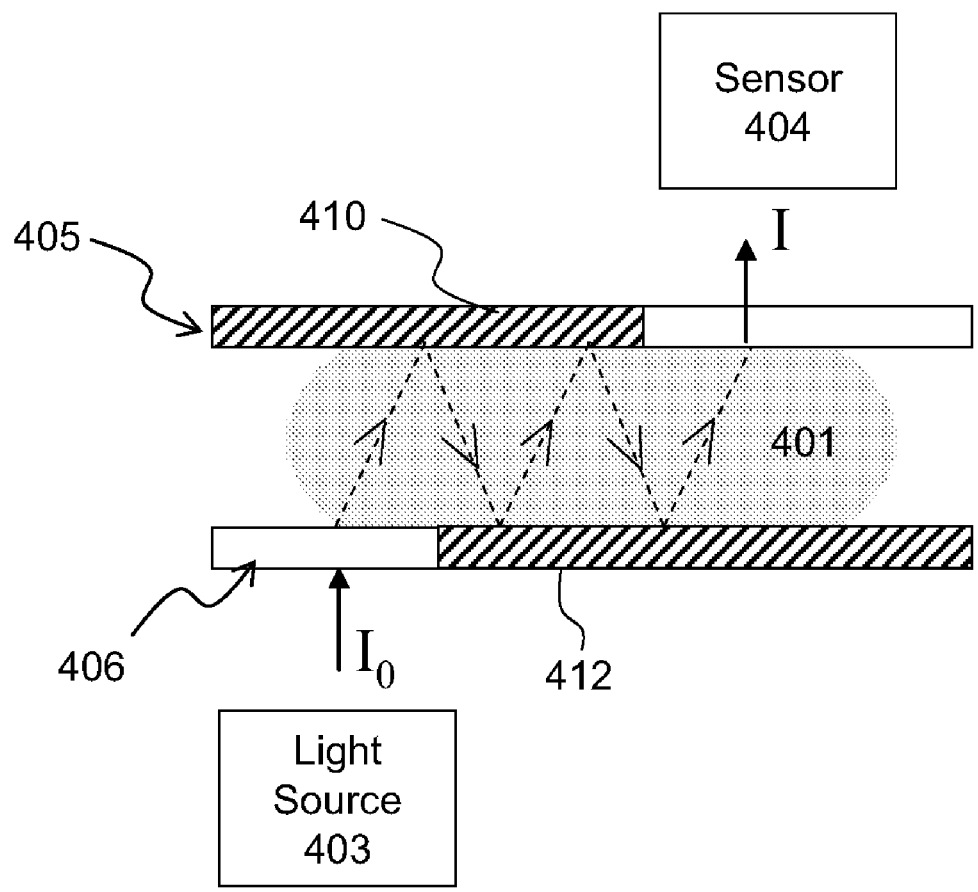

FIG. 4B illustrates an absorbance detection device or configuration of the invention. Both top substrate 405 and bottom substrate 406 include reflective regions 410 and 412, respectively. Light source 403 and sensor 404 are located on opposite side of droplet 401. Reflective surface 412 leaves sufficient opening for light to enter the droplet at one region. Reflective surface 410 leaves sufficient opening for light to enter the droplet at one region. Preferably the distance between entry and exit points is substantially maximized. Light transmitted from light source 403 enters droplet 401 through bottom substrate 406. The light is reflected off of reflective surfaces 410 and 412 through droplet 401 and exits droplet 401 through top substrate 405 to sensor 404. The top and bottom substrates may be reversed in this example.

Figure 4C:
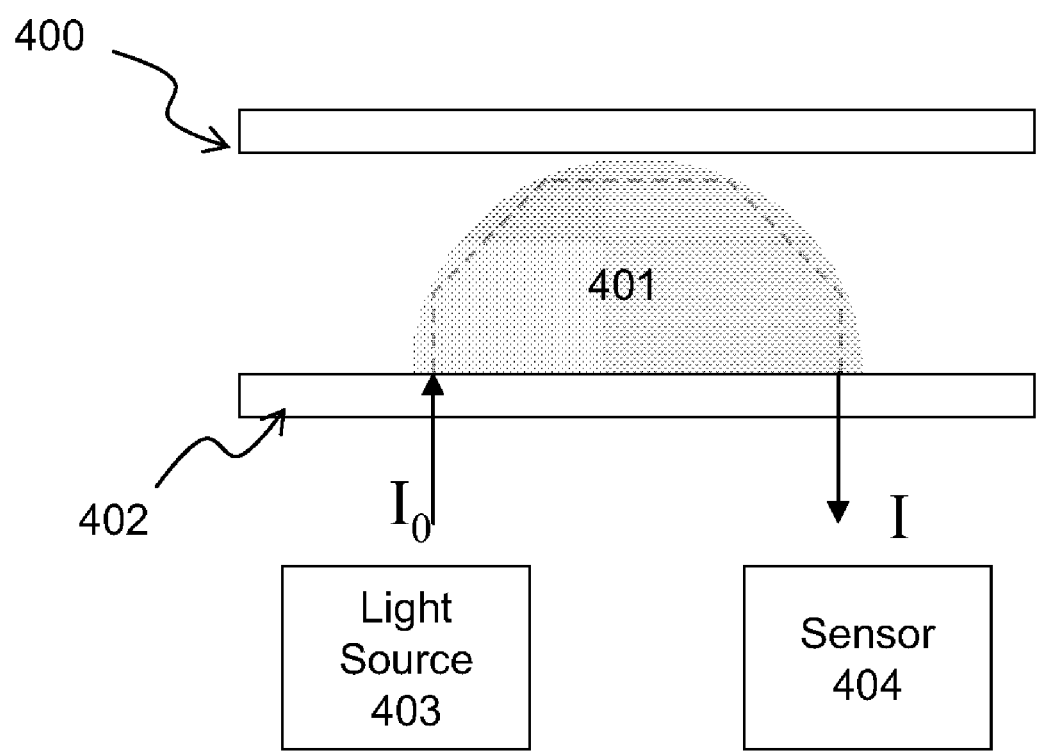

FIG. 4C illustrates an absorbance detection device or configuration of the invention. Bottom surface 402 is at least partially transmissive and/or includes at least partially transmissive regions for entry and exit of light to and from droplet 401. Top surface 400 may or may not be transmissive. In some embodiments, such as the one shown, the distance between top substrate 400 and bottom substrate 402 is selected relative to the droplet and electrode (if any) size and properties to cause droplet 401 to take on a substantial dome or semi-spherical shape. In this manner, light from light source 403 entering one region of droplet 401 through bottom substrate 402 undergoes total internal reflection (TIR), reflecting off the inner surfaces along the curvature of the droplet, and exits in another region of droplet 401 through bottom substrate 402 to detector or sensor 404. In this case, the refractive index of droplet must be greater than that of the surrounding medium for TIR to occur and result in an increased path-length. While FIG. 4C illustrates an embodiment in which droplet shape is symmetrically altered to support TIR, it should also be noted that droplet may be altered asymmetrically. For example, where droplet is being controlled by electrowetting, one side of droplet may have an acute contact angle (wetting) while the other side is obtuse (nonwetting). In this configuration, the source 403 and detector 404 may be orthogonal. For example, this light source may be located on a bottom side of droplet, while sensor is located on the opposite side of droplet.

Figure 5:
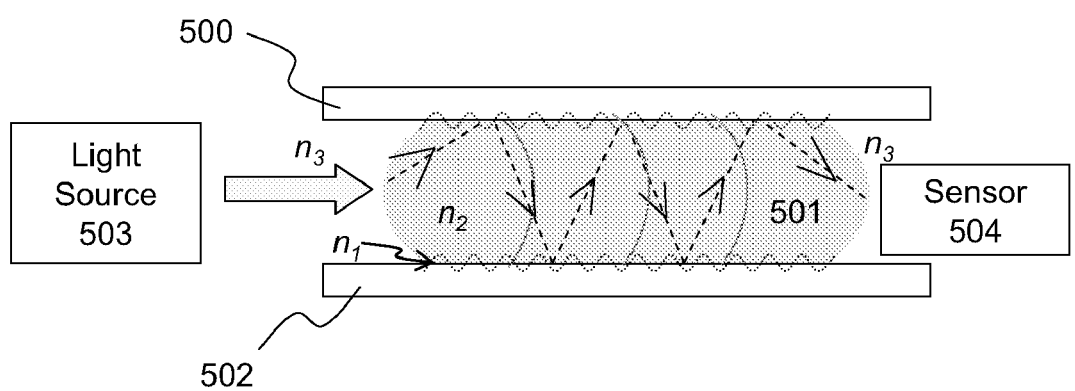
FIG. 5 illustrates an absorbance detection device or configuration of the invention in which the droplet has a higher refractive index as compared to the inner surfaces of the substrates.

FIG. 5 illustrates an absorbance detection device or configuration of the invention. In this embodiment, light transmitted from light source 503 passes through droplet 501 to sensor 504. Droplet 501, which has a higher refractive index as compared to the inner surface of top substrate 500 and bottom substrate 502 and/or as compared to the filler fluid. Droplet 501 operates as a wave guide utilizing the total internal reflection phenomenon, resulting in a greatly increased path-length. The refractive index n2 of droplet 501 is sufficiently greater than the refractive index of top and bottom surfaces n1, and the refractive index of the filler fluid n3 to cause the droplet to function as a waveguide. In other words, $n2 > \{n3, n1\}$.

In an aspect of this embodiment, the length of droplet 501 is greatly increased (e.g., to 10 or 20 droplets), and light transmitted from light source 503 passes through droplet 501 which functions as a wave guide transmitting light to sensor 504.

In another aspect of the embodiment, multiple droplets, such as about 1 to about 30 droplets or about 10 to about 20 droplets, may be added to droplet to change the dynamic range of the detector. If a droplet is too dense or if the absorption needs to be decreased, for example, diluent, buffer or reaction mixture may be added using droplet operations to merge the droplet with one or more additional droplets. The addition of droplets may help obtain a discernable signal. The addition of droplets may occur in real time. For example, if in real time output is measured, and it is determined that the addition of a droplet or droplets would improve the output, then more droplets may be added to achieve sufficient output. On the other hand, if the absorption in the droplet needs to be increased, then the production of absorbing species may be concentrated on the droplet actuator into a small number of droplets using methods for pre-concentration.

Although FIG. 5 shows a non-limiting embodiment in which light source 503 is lateral to droplet 501, the light could be transmitted from the top, bottom or at an angle. If the light is transmitted from the top or bottom, the angle should be below the critical angle to enable the light to go through wave guiding.

Low refractive materials would be used to coat top substrate 500 or bottom substrate 502, for example, or the top substrate 500 and bottom substrate 502 may be made of a low refractive material. Teflon and Cytop are examples of suitable materials with a low refractive index useful in the invention. A filler fluid may also be selected having a refractive index lower than that of droplet.

The embodiments illustrated in FIGS. 1-5 are focused on altering the positioning of light source and detector, and/or altering the refraction of the top or bottom surface. Subsequent embodiments will focus on altering the size of droplet, or combining the embodiments, in which both droplet size and source positioning, detector positioning, and/or refraction of top and bottom surface are altered.

Figure 6:
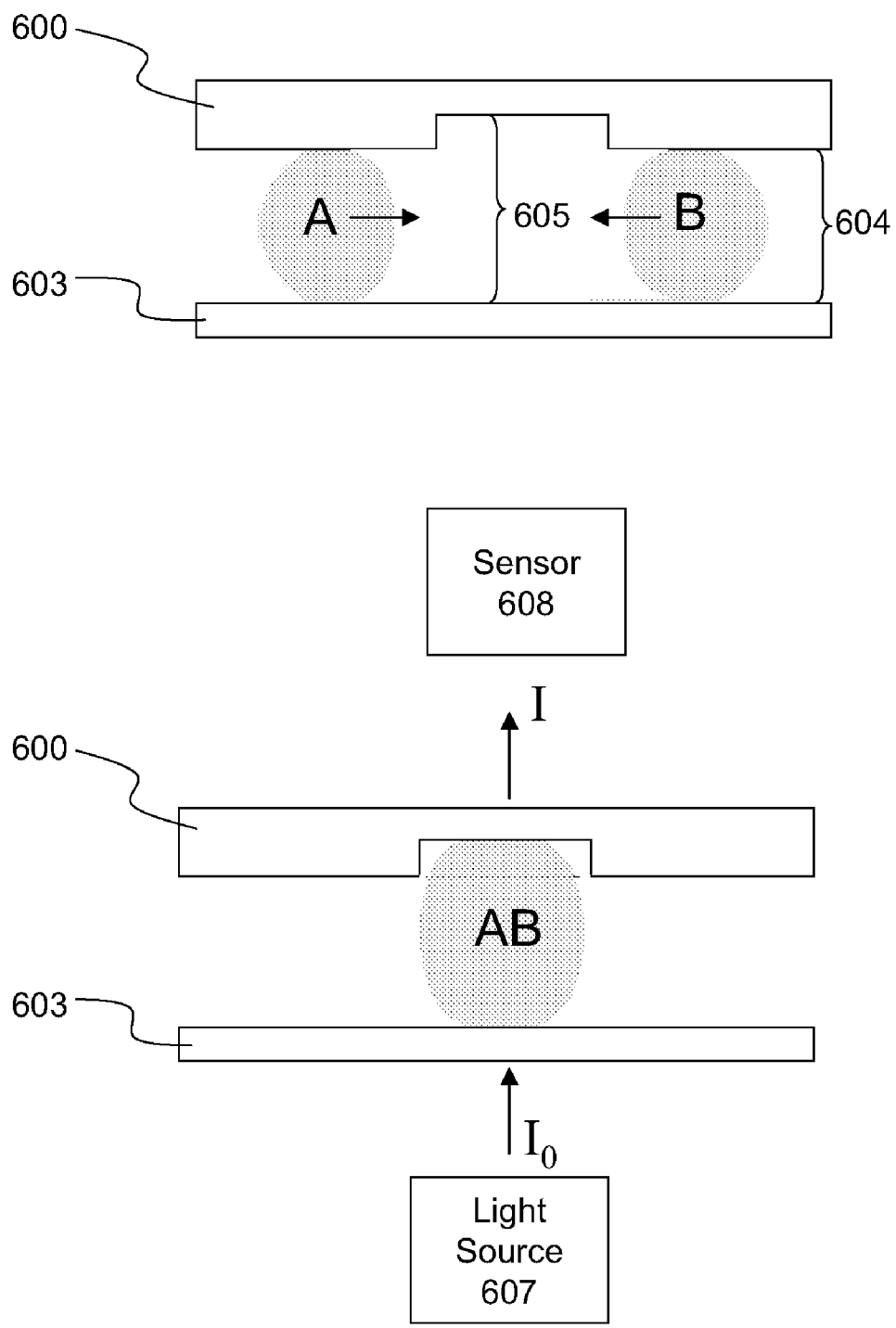
FIG. 6 illustrates an absorbance detection device or configuration of the invention in which path-length of light is increased due to the presence of a recess or gap.

FIG. 6 illustrates an absorbance detection device or configuration of the invention. The path-length of light from light source 607 as it passes through droplet AB to detector or sensor 608 is increased vertically due to the presence of recesses or gaps of different heights in the droplet actuator. The droplet actuator has a first gap 604 of a certain height (such as about 100 µm), and a second gap 605 of a greater height (such as about 500 µm). Droplets A and B are first positioned in the gap 604 of a shorter height. One or more droplets having sufficient volume may be transported into the gap 605. In the example illustrated here, droplets A and B are merged using droplet operations in the gap 605 to yield droplet AB having an increased droplet height relative to the starting droplets. Source 607 and detector 608 are located below and above the gap 605 of greater height. The path-length of light from light source 607 as it passes through droplet AB in the gap 605 of greater height to sensor 608 is increased vertically.

Figure 7:
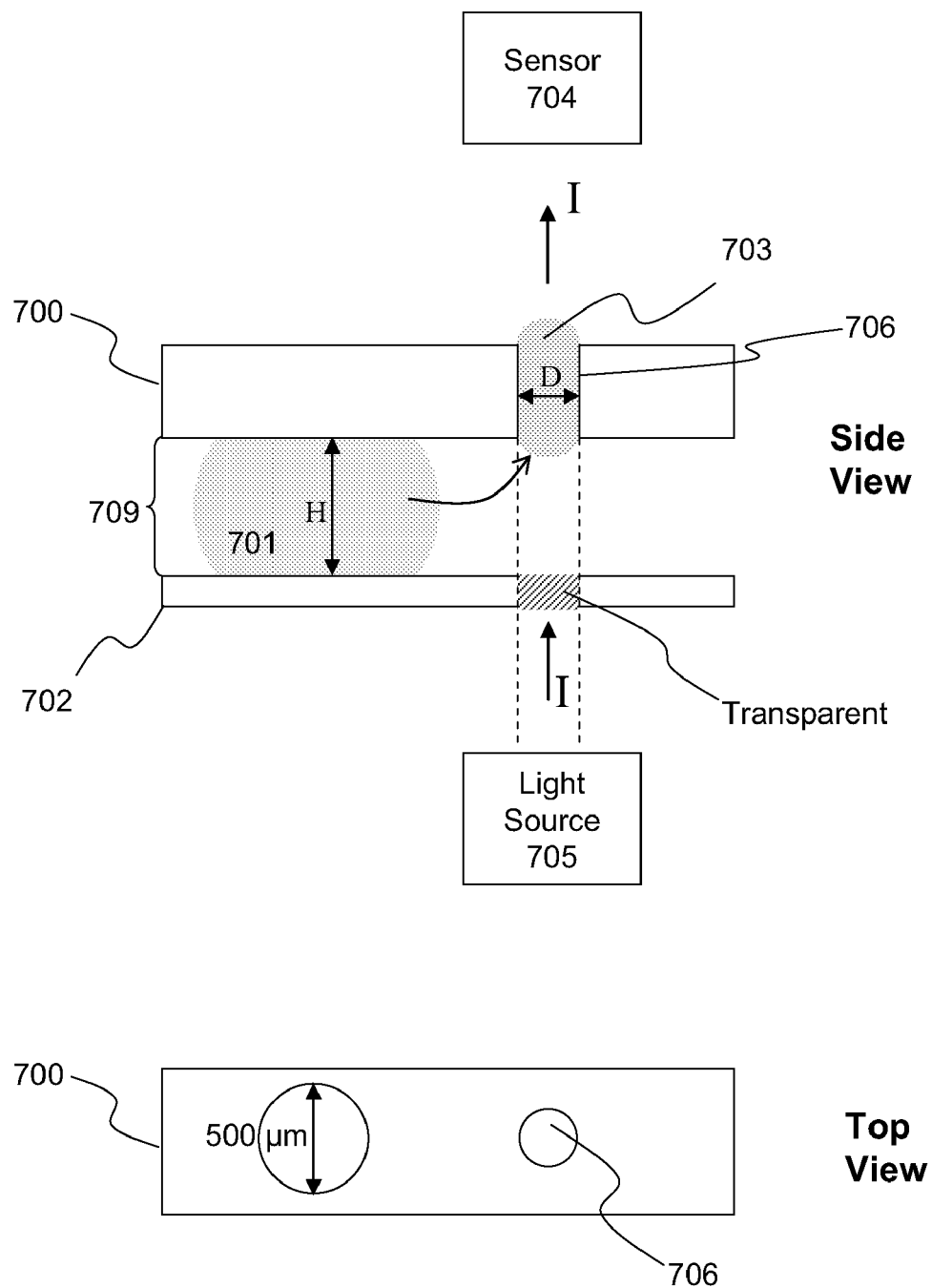
FIG. 7 illustrates an absorbance detection device or configuration of the invention in which an opening is provided in a substrate in order to increase the light path-length.

FIG. 7 illustrates an absorbance detection device or configuration of the invention. In this embodiment, the path-length of light from light source 705 as it passes through droplet 703, in the opening 706, to detector or sensor 704, is increased vertically relative to the droplet height as established by the height of gap 709. The top portion of FIG. 7 shows the side view of the embodiment illustrating top substrate 700 separated from the bottom substrate 702 by gap 709. Gap 709 may contain droplet 701. Top substrate 700 includes an opening 706. Opening 706 may have a volume capacity similar to or larger than the size of droplet 701. Opening 706 may be a capillary. Bottom substrate 702 may include a transparent region which is underneath the opening 706 in line with the light path from light source 705 to sensor 704. The bottom portion of FIG. 7 shows a top view of the embodiment, illustrating opening 706 in top substrate 700. While opening 706 is illustrated here in the top substrate, it should be noted that it may be in the bottom substrate or even in a side wall or other structure of the droplet actuator.

A droplet 701 is placed in droplet actuator. Droplet 701 can be positioned at opening 706 and made to enter 706, e.g., by capillary action, by electrostatic, mechanical or other means. Opening 706 has a diameter selected in relation to the height of gap 709 and size of droplet 701 to cause droplet 701 to passively enter opening 706. If D in the figure is smaller than H, droplet 704 will passively enter opening 706 (note that the figure is not drawn to scale). Light from light source 705 is transmitted through droplet 703 in opening 706 to sensor 704.

Figure 8:
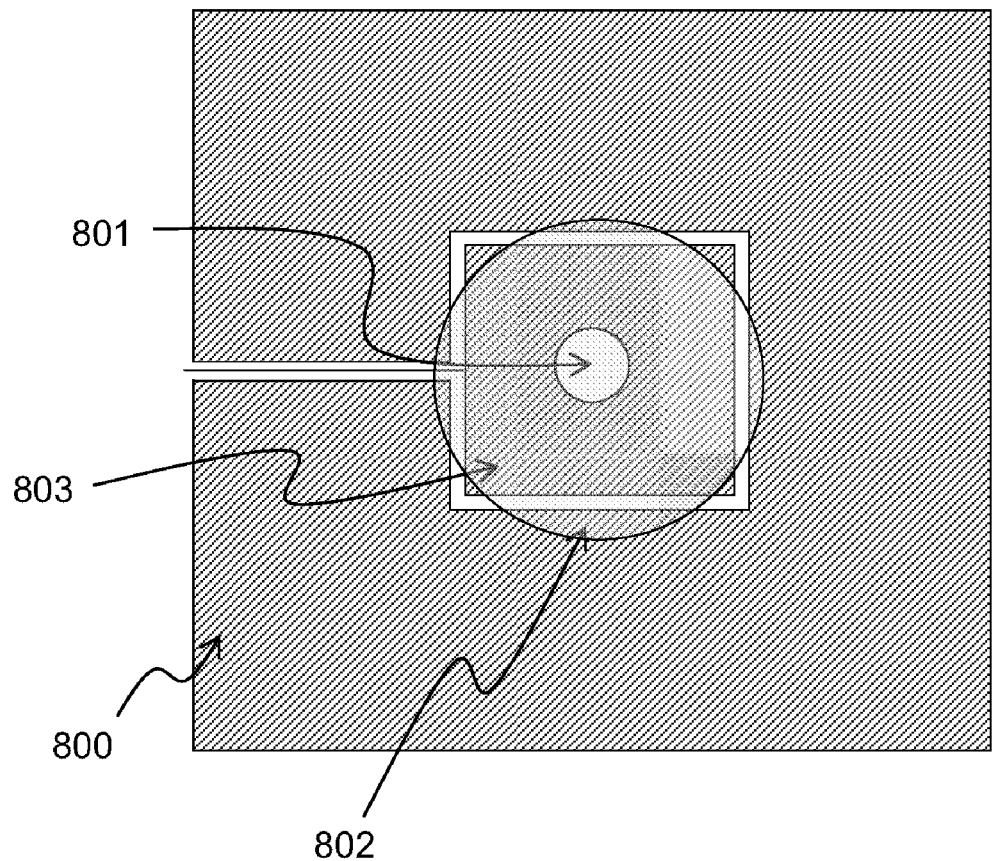
FIG. 8 illustrates a top view of an absorbance detection device or configuration of the invention in which a transparent region is provided in a substrate to allow for light pass-thru.

FIG. 8 illustrates an absorbance detection device or configuration of the invention (top view). In this embodiment, a transparent region 801 is provided in the substrate 800 so that substantially all of the light that reaches the sensor (not shown) is transmitted through droplet 802. Electrode 803 is made using an opaque material, such as aluminum, chrome, copper or other materials used for forming electrodes. Alternatively, an opaque material may be coated onto the electrode or onto the substrate with which the electrode is associated. The opaque material may be on the same surface as electrode 803, or below the droplet actuator, for example. Further, as illustrated, the opaque region may extend to regions of the substrate beyond electrode 803 as needed to fully block light not passing through transparent region 801. Transparent region 801 may be sized to transmit the desired amount of light from a light source (not shown). Transparent region 801 may include one or more transparent regions, and may be an array of transparent regions. Transparent region 801 may contain a diffraction grating or other optical element. The electrode itself may be a diffraction grating Diffractive optics, or other optics such as lenses, may be patterned in the metal or first conductive layer in transparent region 801. Transparent region 801 may be semi-transparent or may include or be comprised of a filter which transmits a desired set of wavelengths. Similarly, the opaque regions may be semi-opaque or may include a filter which excludes a desired set of wavelengths. Such diffractive optics can also be helpful for other forms of optical detection such as in fluorescence and luminescence where optical filters can also be constructed.

Figure 9A:
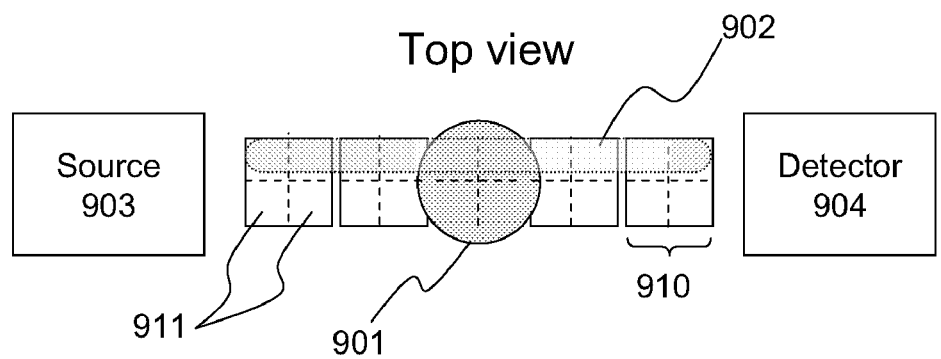
FIGS. 9A and 9B illustrate configurations of an absorbance detection device or configuration of the invention in which a droplet is elongated to provide an elongated light path for detection.

FIG. 9A illustrates an absorbance detection device or configuration of the invention. In this embodiment, a single droplet 901 is elongated to provide an elongated light path for detection. A single droplet can be elongated by addition of multiple droplets or by reducing the size of the unit electrode. In the specific aspect illustrated, each electrode 910 is comprised of multiple smaller electrodes 911. By activating these smaller electrodes in a sequence, droplet 901 can be elongated to form elongated droplet 902. The path-length of light from light source 903 as it passes through droplet 902 to detector or sensor 904 is thereby increased. Different electrodes can be activated to elongate droplet laterally. The source 903 and detector 904 are, in this embodiment, located laterally with respect to droplet. Of course, a similar configuration can be arranged vertically to elongate a droplet in a vertical direction, or in any other spatial orientation.

Figure 9B:
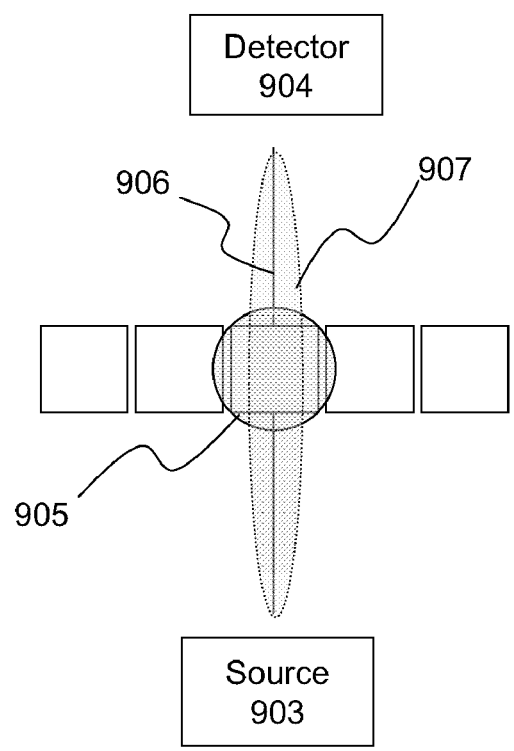

FIG. 9B illustrates an absorbance detection device or configuration of the invention. As illustrated, droplet 905 is elongated in the presence of electric field to form an elongated droplet 907. The path-length of light from light source 903 as it passes through droplet 907 to detector or sensor 904 is thereby increased. Light source 903 and sensor 904 are placed horizontally along the direction of elongation of droplet. The elongated or wire-shaped electrode 906 supplies the field that causes the droplet to generally conform to the shape of electrode 906, thereby forming the elongated droplet 907.

Figure 10A:
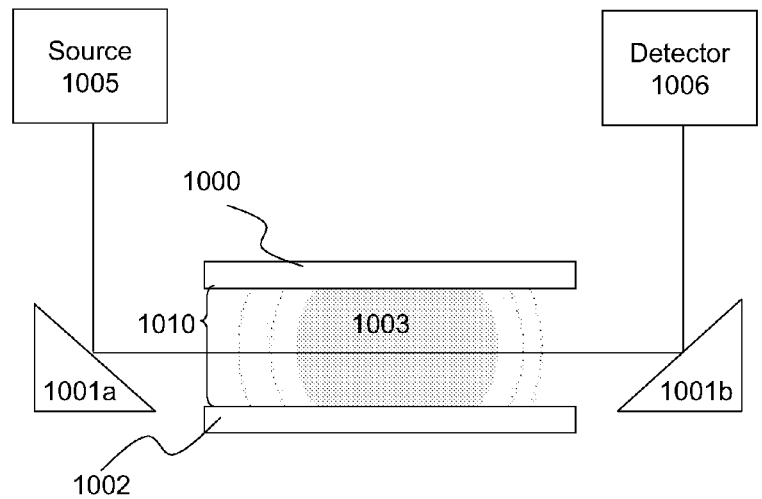
FIGS. 10A-10C illustrates configurations of an absorbance detection device or configuration of the invention in which optical elements are used to transmit light.

FIG. 10A illustrates an absorbance detection device or configuration of the invention. In this embodiment, light source 1005 and detector or sensor 1006 are on the same side of the droplet actuator, and may be in substantially the same plane, but not in the same plane as droplet 1003. Top substrate 1000 is separated from bottom substrate 1002 by gap 1010. Droplet 1003 may be present in gap 1010. Light from light source 1005 is redirected by prism 1001*a* through droplet 1003. Light from droplet 1003 is redirected by prism 1001*b* to sensor 1006. Any optical element used to redirect light, e.g., mirrors, may be used in this configuration. Further, the light source and sensor may be located in any spatial orientation relative to the droplet, so long as the optical elements used to redirect light cause the light to be directed substantially in a direction through the droplet which provides a lengthened light path relative to other possible directions through the droplet by which light could be directed.

Figure 10B:
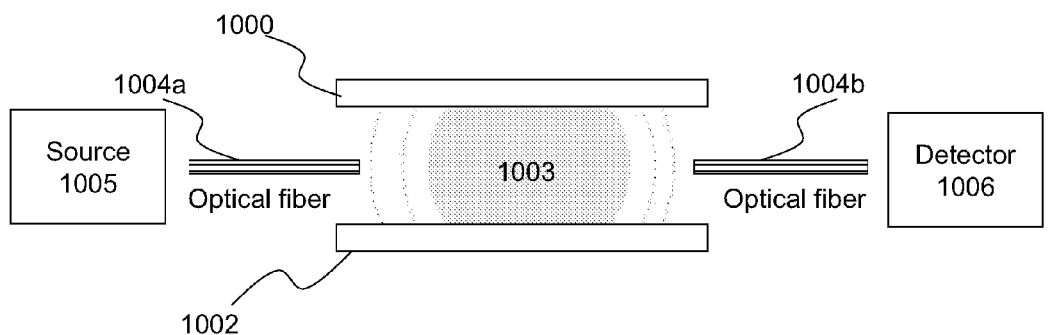

FIG. 10B illustrates an absorbance detection device or configuration of the invention. In this embodiment, light from light source 1005 is transmitted to droplet 1003 using an optical fiber 1004*a* and from droplet 1003 to detector or sensor 1006 using optical fiber 1004*b*.

Figure 10C:
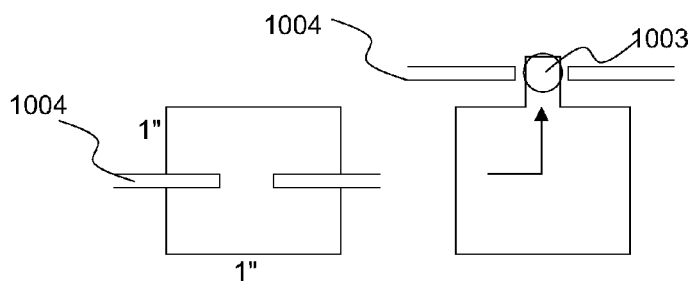

In FIG. 10C, different arrangements of optical fiber 1004 and the droplet actuator are illustrated. For example, a droplet actuator may be constructed which has an extension into which droplet 1003 is positioned. The optical fibers may be configured on either side of the extension feature.

Figure 11:
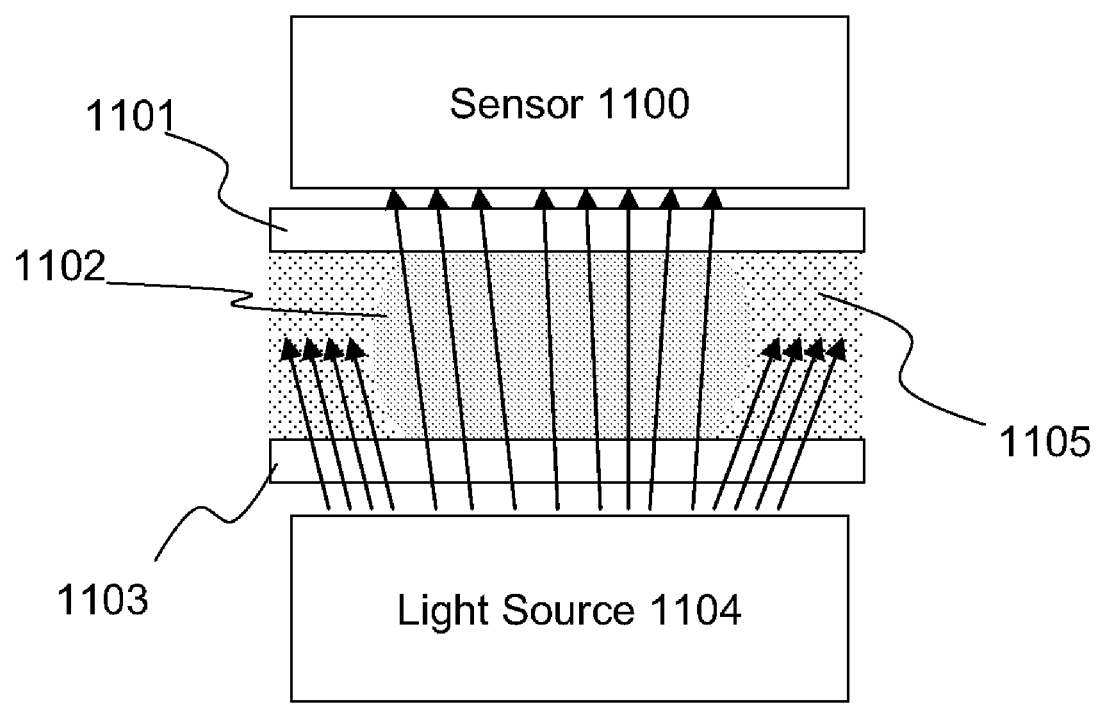
FIG. 11 illustrates an absorbance detection device or configuration of the invention in which dyes or additives are used to absorb light of interest.

FIG. 11 illustrates an absorbance detection device or configuration of the invention. In this embodiment, filler fluid 1105 includes dyes or additives that absorb light of interest. Light from light source 1104 directs light through droplet 1102 to detector or sensor 1100. Some portion of all of the light that does not go through droplet 1102 is absorbed or reflected by filler fluid 1105. This embodiment is particularly suitable for configurations in which light source 1104 and/or detector 1100 is greater in size than droplet 1102. The area surrounding droplet 1102 can be masked with the filler fluid 1105. The filler fluid 1105 may contain a dye or an inverse color filter, the filler fluid 1105 may be opaque, and/or the filler fluid 1105 may have a refractive index to deflect the light away from sensor 1100 and not through droplet 1102.

In a related embodiment, the filler fluid may be an oil, such as a silicone oil, doped with oil-soluble particles to scatter the light from a light-emitting droplet (e.g., fluorescing droplet) so that the droplet's light does not make its way into another droplet.

A variety of dyes may be used in this embodiment. Keystone Aniline makes oil soluble dyes (also fluorescent dyes) that could be used. Black dye, such as carbon black, may be used. Colored silicone oil is also available from Gelest, e.g., DMS-T21BLU and DMS-T21RED.

Other examples of suitable dyes include: Sandoplast Red BB, magenta, sudan I, sudan II, sudan III, and sudan IV, oil red O, and Nile red.

In one embodiment, the oil soluble dye also serves as a surfactant.

8.1 Light Source and Detectors

In the above embodiments, any monochromatic light source may be used with a filter. LEDs which are tuned to the wavelength of the measured dye in droplet are useful. Lasers may be useful. Detectors or sensors may be silicon, photodiode, multiple photodiodes, photodiode arrays, single sensors, or additional CCD, avalanche photodiodes, PMT (photo multiplier tube), photon counting PMTs or any other low noise detectors, for example. Examples of light sources, detectors and configurations are provided in International Patent Application No. PCT/US2006/47486, entitled "Droplet-Based Biochemistry," filed on Dec. 11, 2006, the disclosure of which is incorporated herein by reference. It will be appreciated that while the disclosure is focused on detection of absorbance of a droplet, many of the configurations will also be suitable for enhancing detection of fluorescence and/or luminescence of a droplet.

8.2 Droplet Actuator

For examples of droplet actuator architectures suitable for use with the present invention, see U.S. Pat. No. 6,911,132, entitled "Apparatus for Manipulating Droplets by Electrowetting-Based Techniques," issued on Jun. 28, 2005 to Pamula et al.; U.S. patent application Ser. No. 11/343,284, entitled "Apparatuses and Methods for Manipulating Droplets on a Printed Circuit Board," filed on filed on Jan. 30, 2006; U.S. Pat. Nos. 6,773,566, entitled "Electrostatic Actuators for Microfluidics and Methods for Using Same," issued on Aug. 10, 2004 and 6,565,727, entitled "Actuators for Microfluidics Without Moving Parts," issued on Jan. 24, 2000, both to Shenderov et al.; and Pollack et al., International Patent Application No. PCT/US2006/47486, entitled "Droplet-Based Biochemistry," filed on Dec. 11, 2006, the disclosures of which are incorporated herein by reference. Gap heights are preferably from 10's μm to 1's cm and more preferably from 100's μm to 10's mm and most preferably from 100's μm to 1's mm. Electrode dimensions preferably in 10's μm, more preferably in 100's μm, most preferably in the range of 10 mm to 1000's μm.

8.3 Fluids

For examples of sample fluids useful according to the approach of the invention, see the patents listed in section 8.2, especially International Patent Application No. PCT/US2006/47486, entitled "Droplet-Based Biochemistry," filed on Dec. 11, 2006. In some embodiments, the fluid includes a biological sample, such as whole blood, lymphatic fluid, serum, plasma, sweat, tear, saliva, sputum, cerebrospinal fluid, amniotic fluid, seminal fluid, vaginal excretion, serous fluid, synovial fluid, pericardial fluid, peritoneal fluid, pleural fluid, transudates, exudates, cystic fluid, bile, urine, gastric fluid, intestinal fluid, fecal samples, fluidized tissues, fluidized organisms, biological swabs and biological washes.

8.4 Filler Fluids

The gap will typically be filled with a filler fluid. The filler fluid may, for example, be a low-viscosity oil, such as silicone oil; or a gas, such as air or an inert gas. Other examples of filler fluids are provided in International Patent Application No. PCT/US2006/47486, entitled "Droplet-Based Biochemistry," filed on Dec. 11, 2006, the entire disclosure of which is incorporated herein by reference.

9 CONCLUDING REMARKS

The foregoing detailed description of embodiments refers to the accompanying drawings, which illustrate specific embodiments of the invention. Other embodiments having different structures and operations do not depart from the scope of the present invention.

This specification is divided into sections for the convenience of the reader only. Headings should not be construed as limiting of the scope of the invention.

It will be understood that various details of the present invention may be changed without departing from the scope of the present invention. Furthermore, the foregoing description is for the purpose of illustration only, and not for the purpose of limitation, as the present invention is defined by the claims as set forth hereinafter.

We claim:

1. A method of determining the absorbance of a droplet, the method comprising:
   (a) providing a droplet actuator comprising:
      (i) two substrates separated to form a gap; and
      (ii) a droplet positioned in the gap and having a droplet height established by surfaces of the two substrates;
   (b) providing a light source arranged to transmit light through the droplet and a sensor arranged to sense light from the droplet, thereby creating a light path through the droplet and substantially parallel with the surfaces of the substrates wherein the light path through the droplet is greater than the droplet height, and further wherein the droplet is arranged in the gap in the ligth path of the light source, wherein:
      (i) the droplet comprises beads; and
      ii) the optical property of the droplet is indicative of an optical property of the beads;
   (c) directing light from the light source through the droplet and to the sensor;
   (d) sensing the light energy at the sensor; and
   (e) using a processor, determining from the sensed light energy an optical property of the droplet.

2. The method of claim 1 wherein the path through the droplet is less than 1 cm.

3. A method of determining the absorbance of a droplet, the method comprising:
   (a) providing a droplet actuator comprising:
      (i) two substrates separated to form a gap; and
      (ii) a droplet positioned in the gap and having a droplet height established by surfaces of the two substrates;
   (b) providing a light source arranged to transmit light through the droplet and a sensor arranged to sense light from the droplet, thereby creating a light path through the droplet wherein the light path through the droplet is greater than the droplet height, and further wherein the droplet is arranged in the gap in the light path of the light source, wherein:
      (i) the droplet comprises biological cells; and
      (ii) the optical property of the droplet is indicative of an optical property of the biological cells;
   (c) conducting droplet operations which elongate the droplet along the light path through the droplet;
   (d) directing light from the light source through the droplet and to the sensor;
   (e) sensing the light energy at the sensor; and
   (f) using a processor, determining from the sensed light energy an optical property of the droplet.

4. The method of claim 3 wherein the path through the droplet is less than 1 cm.

5. The method of claim 3 wherein the elongating comprises positioning the droplet within an aperture of a substrate, thereby increasing the droplet height.

6. The method of claim 3 further comprising elongating the droplet along a central axis of the droplet defined by the path of light using an electrode.

7. The method of claim 3 wherein the light path through the droplet is substantially perpendicular to the droplet height and/or surfaces of the substrates.

8. The method of claim 3 wherein the light path through the droplet is at an angle that is substantially acute with respect to one of the surfaces establishing the droplet height.

9. The method of claim 3 wherein the elongating comprises conducting a droplet operation which increases the height of the droplet.

10. The method of claim 3 further comprising:
(a) a droplet in the gap in a path of the light source; and
(b) filler fluid surrounding the droplet.

11. The method of claim 3 wherein the droplet comprises beads, and the optical property of the droplet is indicative of an optical property of the beads.

12. The method of claim 3 wherein the droplet comprises biological cells, and the optical property of the droplet is indicative of an optical property of the biological cells.

* * * * *